(12) United States Patent
Coleman

(10) Patent No.: US 6,884,917 B1
(45) Date of Patent: Apr. 26, 2005

(54) 1-BUTENE PRODUCTION

(75) Inventor: Steven T. Coleman, Humble, TX (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 10/848,414

(22) Filed: May 18, 2004

(51) Int. Cl.⁷ .............................................. C07C 6/00
(52) U.S. Cl. ........................................ 585/643; 585/646
(58) Field of Search .................................. 585/643, 646

(56) References Cited

U.S. PATENT DOCUMENTS

| | | | |
|---|---|---|---|
| 5,698,760 A | 12/1997 | Kelly ......................... | 585/643 |
| 6,166,279 A | * 12/2000 | Schwab et al. ............. | 585/324 |

OTHER PUBLICATIONS

R. L. Banks, *Journal of Molecular Catalysis*, vol. 8, p. 269–276, 1980, ISSN 0304–5102.

Robert L. Banks, "Discovery and Development of Olefin Disproportionation (Metathesis)," American Chemical Society Symposium, Series, No. 222, Heterogeneous Catalysis: Selected American Histories, B.H. Davis and W. P. Hettinger, Jr., Editors, *American Chemical Society*, 1983, ISSN 0097–6156.

* cited by examiner

*Primary Examiner*—Thuan D Dang
(74) *Attorney, Agent, or Firm*—Roderick W. MacDonald

(57) ABSTRACT

A method for forming high purity 1-butene wherein a feed composed of pentenes and hexenes is subjected to metathesis with ethylene to form a mixture containing propylene, 1-butene, 2-butenes, pentenes, and hexenes, and high purity 1-butene is separately recovered from the mixture by simple distillation.

10 Claims, 1 Drawing Sheet

1-BUTENE PRODUCTION

BACKGROUND OF THE INVENTION

1. Field of the Invention

This invention relates to the production of 1-butene, and, in particular, the production of high purity 1-butene.

2. Description of the Prior Art

Heretofore, high purity 1-butene has traditionally been produced from a mixture of hydrocarbons having 4 carbon atoms per molecule (C4s). The desired 1-butene was distilled from this C4 mixture.

This C4 mixture was obtained from a plurality of varying processes. One exemplary process is the thermal cracking of a hydrocarbon stream in an olefin production plant. Thermal cracking of hydrocarbons is a petrochemical process that is widely used to produce olefins such as ethylene, propylene, butenes, butadiene, and aromatics such as benzene, toluene, and xylenes. In an olefin production plant, a hydrocarbon feedstock such as naphtha, gas oil, or other fractions of whole crude oil is mixed with steam which serves as a diluent to keep hydrocarbon molecules separated. This mixture, after preheating, is subjected to hydrocarbon thermal cracking at elevated temperatures of from about 1,450 degrees Fahrenheit (F or ° F.) to about 1,550F in a pyrolysis furnace (steam cracker).

The cracked product from the pyrolysis furnace contains gaseous hydrocarbons of great variety (from 1 to 35 carbon atoms per molecule, inclusive). This product contains aliphatics, aromatics, saturates, and unsaturates, and can contain significant amounts of molecular hydrogen (hydrogen).

This cracked product is then further processed in the olefin plant to produce, as products of the plant, various separate streams such as hydrogen, ethylene, propylene, pyrolysis gasoline, and a crude C4 stream. This C4 stream can contain varying amounts of n-butane, isobutane, 1-butene, 2-butenes (both cis and trans isomers), isobutylene, acetylenes, butadienes (cis and trans isomers), and hydrogen.

Heretofore, this crude C4 stream has been subjected to hydrogenation to remove acetylenes, extractive distillation to remove diolefins such as butadiene isomers, and an etherification step to convert at least some of the isobutylene to methyl t-butyl ether. The methyl t-butyl ether is separated as a product of the process thereby leaving a separate raffinate product that contains 1-butene, 2-butenes, isobutane, n-butane and, at most, only traces of butadienes and isobutylene. As disclosed in detail later, the raffinate components other than 1-butene are all close boiling to 1-butene, and 1-butene is in the middle of the relevant boiling range. For example, isobutane is lighter (boils at a lower temperature) than 1-butene, whereas n-butane and 2-butenes are heavier (boil at a higher temperature) than 1-butene. Also 1,3 butadiene and isobutylene boil especially close to 1-butene, and, therefore, are troublesome even in trace amounts when the goal is high purity 1-butene. This is recognized in U.S. Pat. No. 5,698,760 to Kelly which is discussed in detail hereinafter.

Also heretofore, this raffinate product has been subjected to metathesis of its 2-butene content with ethylene to form propylene. After the separate removal of ethylene for recycle to the metathesis zone and propylene as a product of the process, the resulting stream contains a substantial amount of 2-pentenes (80 to 90 weight percent (wt %) based on the total weight of the stream), the remainder being a mixture of 1-pentene, 1-butene, 2-butenes, and trace amounts of hydrocarbons having 6 carbon atoms per molecule (C6s). A mixture of butenes, n-butane, and isobutane has been removed from this stream and sent on to alkylation or thermal cracking due to its n-butane and isobutane content, leaving a separate mixture of 2-pentenes (cis and trans isomers) in the amount of at least about 80 wt % based on the total weight of the separate mixture, up to about 15 wt % 1-pentene, and up to about 5 wt % C6s. This invention can employ as its feed material this mixture of 2-pentenes, 1-pentene, and C6s. This mixture does not contain 2-methylbutene-2 which is required by the Kelly patent cited above. As disclosed in greater detail hereinafter, other streams containing hydrocarbons having 5 carbon atoms per molecule (C5s), including significant amounts of both 2-pentenes and C6s, can be used as a feed material for this invention.

The prior art has deliberately made mixtures of 1-butene and isobutylene, see the Kelly patent cited above. In this patent the required feed material for the process is, at a minimum, a mixture of 2-pentene, 2-methylbutene-2, and C6s. This feed material is then subjected to a deep, selective hydrogenation and fractionation process to remove essentially all of the C6s, and to substantially increase (double) its 2-pentene and 2-methylbutene-2 content over that of the original feed material. The product of this hydrogenation/fractionation process contains substantial amounts of the required 2-pentene (greater than 15 wt %) and 2-methybenzene-2 (greater than 17 wt %), and no C6s. This product is then subjected to metathesis with ethylene to form a final product containing primarily 1-butene, isobutylene, and propylene. The propylene is separated as a product of the process leaving an end mixture of 1-butene and isobutylene as a co-product. The patent states that this mixture of 1-butene and isobutylene "is difficult to separate by simple fractionation due to the close proximity of their boiling points", i.e., less than 1 degree F. The patent then suggests separation techniques such as an alcohol reaction or absorption for separating 1-butene from isobutylene which are more complicated and expensive than simple distillation. In contrast to the Kelly patent, the instant invention tolerates C6s in its feed material, does not require the separation of C6s there from, and does not make isobutylene from 2-methylbutene-2. This invention provides an end mixture containing C4s, C5s, and C6s from which high purity 1-butene can readily be separated by way of simple, low-cost distillation. This is so because no isobutylene, butadiene (particularly 1,3 butadiene), isobutane, or n-butane is present in the end mixture to be distilled, the nearest boiling compound to 1-butene in this end mixture being 2-butenes, both of whose isomers have a boiling point (b.p.) more than 10F higher than 1-butene. A boiling point separation between two compounds of more than 10 degrees F. readily allows for separation of those compounds by low-cost, simple distillation.

SUMMARY OF THE INVENTION

In accordance with this invention there is provided a process for making 1-butene wherein 2-pentenes (both cis and trans isomers) are metathesized with ethylene to form a mixture containing ethylene, propylene, 1-butene, and no C4s having a boiling point closer to the boiling point of 1-butene than 2-butenes, separating ethylene and propylene from the mixture, and then separating 1-butene from the remainder of the mixture using simple distillation.

BRIEF DESCRIPTION OF THE DRAWINGS

The sole

DETAILED DESCRIPTION OF THE INVENTION

Figure 1:
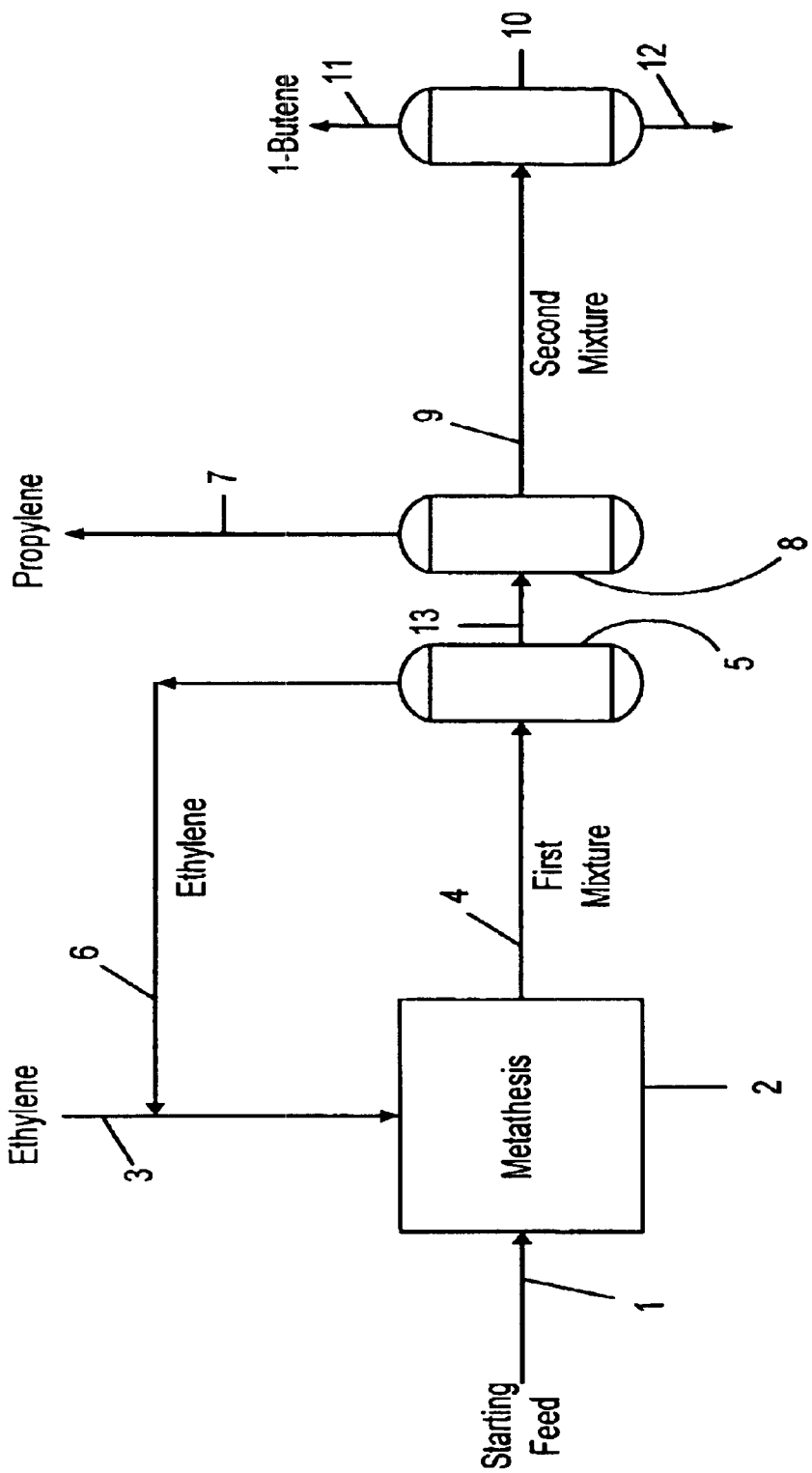
FIG. 1 shows one embodiment within this invention.

This invention revolves around the facts that 1-butene, having a b.p. of about 20.6F,
1) boils within about 1 degree F. of isobutylene (b.p. about 19.5F),
2) boils within about 3 degrees F. of 1,3 butadiene (b.p. about 23.9F),
3) boils below isobutane (b.p. about 10.4F).

As recognized by the Kelly patent cited above, 1-butene is extremely difficult to separate from isobutylene by simple distillation, their boiling points being less than 1 degree F. apart. By a similar boiling point comparison, 1-butene is difficult to separate from butadiene by simple distillation. Separation of 1-butene by simple distillation is complicated by the presence of isobutane since isobutane is lighter than 1-butene. Being lighter, isobutane will boil (distill) off before 1-butene thereby contaminating the overhead product of the distillation tower that is to contain the desired 1-butene in pure form. The term "simple distillation" as used herein means separation of chemical compounds (components) using a basic thermal distillation tower which relies primarily only on the relative boiling points of the compounds to be separated. It is straight forward boiling point fractionation using a distillation tower without assistance, e.g., by way of catalyst or the like. It does not involve more complicated and expensive separation processes such as a chemical reaction, e.g., an alcohol reaction; absorption; and the like.

Referring to the drawing, in accordance with this invention a mixture of C5s, primarily pentenes, and C6s, primarily hexenes, is employed as starting feed material 1. Feed 1 can contain at least about 80 wt % 2-pentenes, and at least about 15 wt % 1-pentene with the remainder being essentially C6s such as 3-hexene, all wt % based on the total weight of feed 1.

Feed 1 is passed into a conventional disproportionation zone 2 wherein it is subjected to metathesis conditions in the presence of ethylene, which conditions favor the disproportionation of internal olefins with ethylene thereby to convert at least part of the 2-pentenes present to propylene. This step produces a first mixture 4 that contains ethylene, propylene, 1-butene, 2-butenes (cis and trans), 1-pentene, 2-pentenes (cis and trans), and hexenes such as 3-hexenes (cis and trans). Mixture 4 contains none of the compounds that are often present and boil very close to 1-butene, e.g., butadiene isomers and isobutylene; and none of the relatively close boilers to 1-butene, e.g., n-butane (b.p. about 31.1F), isobutane, or acetylenes such as vinyl acetylene or ethyl acetylene. Mixture 4 can routinely contain at least about 50 wt %, based on the total weight of the mixture, of propylene and 1-butene, the propylene and 1-butene being present in about equal amounts on a molar basis.

Ethylene is removed from mixture 4 by simple distillation tower 5 for recycle 6 as feed to metathesis zone (step) 2. Propylene 7 is also separated by a simple distillation tower 8, and removed as an individual product of the process.

This leaves as a remainder from first mixture 4, a second mixture 9 which are composed of 1-butene, 2-butenes, 1-pentene, 2-pentenes, and small amounts of hexenes such as 3-hexenes. Mix 9 contains no very close or even relatively close boilers to 1-butene as defined here in above. The closest boilers to 1-butene in mixture 9 are 2-butenes (trans-2-butene b.p. of about 33.8F and cis-2-butene b.p. of about 38.6F).

The separation of 1-butene from 2-butenes in second mixture 9 can readily be accomplished by a simple distillation tower 10 which is relatively economic to operate. Consequently, a high purity 1-butene product 11 can be separated from mixture 9 as an individual product of the process. High purity product 11 will contain no n-butane, isobutane, isobutylene, butadienes or acetylenes. Product 11 is recovered as overhead from tower 10. Tower bottoms 12 contain the remaining 2-butenes, pentenes, and hexenes.

It can be seen that the process of this invention is advantageous in that bottoms 12 has a minimum of heavy (higher boiling) components. Also, it will be obvious to those skilled in the art that 2-butenes can, if desired, readily be separated by simple distillation from the pentenes and hexenes present in bottoms 12.

Feed 1 can come from a number of disparate sources within an olefin plant, oil refinery, or the like. For example, in addition to the raffinate product described in detail here in above, feed 1 can come from the known process of dimerizing ethylene to a mixture of 1-butene and 2-butenes after removal of hexenes therefrom. The product of the ethylene dimerization step is then subjected to conventional metathesis with ethylene to form propylene from at least part of the 2-butenes present. This metathesis operation is totally separate from metathesis step 2 of FIG. 1, and, therefore, is referred to as dimerization mode metathesis. Dimerization mode metathesis not only forms propylene from the combination of ethylene and 2-butenes, but also forms propylene from the combination of 1-butene with 2-butenes. This latter combination also forms some 2-pentenes. The product of dimerization mode metathesis is then distilled to remove both ethylene and propylene as separate products thereby leaving a mixture of C4s and C5s with small amounts of C6s. The C4s are separated by way of distillation, and recycled to extinction in the dimidiation mode metathesis step thereby leaving a mixture of 1-pentene, 2-pentanes, and hexanes such as 3-hexane that is suitable for use as feed 1. An advantage of using this ethylene dimidiation mode is one skilled in the art can shift emphasis, as desired, on producing more propylene or more pentenes by simply shifting the amount of ethylene fed to the metathesis unit. For example, less ethylene feed to the dimerization mode metathesis unit will produce more pentenes, while more ethylene feed will produce more propylene product.

Feed 1 can also be a C5 containing stream recovered from a fluid catalytic cracking operation, a resid/heavy oil coking process, the dehydrogenation of n-pentane, and the like.

Bottoms 12 can be recycled to metathesis step 2, if feed 1 is derived from ethylene dimerization or raffinate, both as described here in above. However, because of the presence of small amounts of n-pentane, bottoms 12 should not be recycled to metathesis step 2 if feed 1 was derived from a fluid catalytic cracker, resid/heavy oil coker, or pentane dehydrogenator.

The metathesis operations for both the metathesis step 2 of this invention and the dimerization mode metathesis are known and fall into the same operating condition ranges. Such operating conditions can vary widely, but will generally be a temperature of from about 300 to about 800F, a pressure of from about 200 to about 600 psig, and a weight hourly space velocity in reciprocal hours of from about 1.0 $h^{-1}$ to about $100^{-1}$.

Suitable catalysts that promote, preferably primarily promote, metathesis as described herein for unit 2 and dimerization mode metathesis are also known in the art, and include at least one of halides, oxides and/or carbonyls of at least one of molybdenum, tungsten, rhenium and/or magnesium carried on a support such as silica and the like. The conversion of internal olefins in the presence of excess ethylene to propylene is known and has been demonstrated; see R. L. Banks, Journal of Molecular Catalysis, Vol. 8, p. 269–276, 1980, ISSN 0304-5102. For more information on olefin metathesis, see Discovery and Development of Olefin Disproportionation (Metathesis) by Robert L. Banks, American Chemical Society Symposium Series, No. 222, Heterogeneous Catalysis: Selected American Histories, B. H. Davis and W. P. Hettinger, Jr., Editors, American Chemical Society, 1983, ISSN 0097-6156.

Ethylene can be distilled at tower 5 from stream 4 using a conventional distillation tower under a pressure of from about 300 to about 400 psig with an overhead temperature of from about minus 20 to about 0° F. Ethylene is removed from the process as a separate and individual product of the process.

After ethylene removal, propylene can be distilled at tower 8 from the remainder 13 of stream 4 using a conventional distillation tower under a pressure of from about 100 to about 300 psig with an overhead temperature of from about 50 to about 125° F. Propylene is removed from the process as a separate and individual product of the process.

After propylene removal, 1-butene can be distilled at tower 10 from the remainder of stream 4 (said second mixture) using a conventional distillation tower under a pressure of from about 10 to about 60 psig with an overhead temperature of from about 60 to about 125° F. The 1-butene product of this invention contains at least about 99 wt % 1-butene based on the total weight of stream 11, and is removed from the process as a separate and individual high purity product of the process.

EXAMPLE

A feed material consisting essentially of about 80 wt % 2-pentenes, about 15 wt % 1-butene, and about 5 wt % 3-hexene, all wt % based on the total weight of the feed is passed into a metathesis zone wherein it is contacted with a molar excess of ethylene in the presence of a commercially available metathesis catalyst composed of a mixture of tungsten oxide and magnesium oxide at a temperature of about 625° F. and a pressure of about 400 psig. The weight hourly space velocity is about 8 $h^{-1}$.

The product of the metathesis operation is a mixture consisting essentially of 50 wt % propylene and 1-butene, the propylene and 1-butene being present in essentially equal amounts on a mol basis, with the remainder being essentially ethylene, 2-butenes, 1-pentene, and 2-pentenes.

Ethylene is distilled from the mixture at about 350 psig pressure with an overhead temperature of about minus 10° F.

After ethylene removal, propylene is distilled from the remainder of the mixture at about 250 psig pressure with an overhead temperature of about 110° F.

After propylene removal the remainder of the mixture consists essentially of 1-butene, 2-butenes, 1-pentene, and 2-pentenes.

The 1-butene is distilled from this remainder at about 55 psig pressure with an overhead temperature of about 110° F., whereby a high purity 1-butene product containing at least 99 wt % 1-butene based on the total weight of the product is obtained and removed from the process as an individual product thereof.

Reasonable variations and modifications are possible within the scope of this disclosure without departing from the spirit and scope of this invention.

I claim:

1. A method for recovering high purity 1-butene using simple distillation comprising providing a feed material consisting essentially of 1-pentene, 2-pentenes, and hexenes, subjecting said feed to metathesis operating conditions with ethylene to convert at least part of said 2-pentenes to a mixture of propylene and 1-butene and produce a first mixture consisting essentially of unconverted ethylene, propylene, 1-butene, 2-butenes, 1-pentene, 2-pentenes and hexenes and containing essentially no isobutylene or butadienes, separating ethylene and propylene from said first mixture thereby leaving a second mixture consisting essentially of 1-butene, 2-butenes, 1- and 2-pentenes, and hexenes, subjecting said second mixture to simple distillation whereby high purity 1-butene is recovered overhead as a product of the process, and leaving a bottom fraction consisting essentially of 2-butenes, 1- and 2-pentenes, and hexenes.

2. The method of claim 1 wherein said feed material contains at least about 80 wt % 2-pentenes, at least about 15 wt % 1-pentene, and the remainder being essentially hexenes, all wt % being based on the total weight of the feed.

3. The method of claim 2 wherein said hexenes consist essentially of 3-hexenes.

4. The method of claim 3 wherein said first mixture contains at least about 50 wt % based on the total weight of the mixture of propylene and 1-butene.

5. The method of claim 4 wherein said propylene and 1-butene are present in about equal amounts on a mol basis.

6. The method of claim 1 wherein said metathesis conditions are a temperature of from about 300 to about 800F, a pressure of from about 200 to about 600 psig, and a weight hourly space velocity of from about 1.0 $h^{-1}$ to about 100 $h^{-1}$ using a catalyst composed of at least on of halides, oxides and carbonyls of at least one of molybdenum, tungsten, rhenium, and magnesium carried on a support.

7. The method of claim 1 wherein said ethylene and propylene are separated individually by simple distillation.

8. The method of claim 1 wherein said bottoms fraction is recycled as feed to said metathesis operation for reuse therein.

9. The method of claim 1 wherein said feed material is derived from a raffinate obtained from a crude C4 stream.

10. The method of claim 1 wherein said feed material is obtained from butenes derived from an ethylene dimerization operation.

* * * * *